United States Patent
Perez

(10) Patent No.: US 11,733,881 B2
(45) Date of Patent: Aug. 22, 2023

(54) INTRALUMINAL DEVICE REUSE PREVENTION WITH PATIENT INTERFACE MODULE AND ASSOCIATED DEVICES, SYSTEMS, AND METHODS

(71) Applicant: KONINKLIJKE PHILIPS N.V., Eindhoven (NL)

(72) Inventor: Cesar Perez, Roseville, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 534 days.

(21) Appl. No.: 16/756,354

(22) PCT Filed: Oct. 17, 2018

(86) PCT No.: PCT/EP2018/078381
§ 371 (c)(1),
(2) Date: Apr. 15, 2020

(87) PCT Pub. No.: WO2019/076971
PCT Pub. Date: Apr. 25, 2019

(65) Prior Publication Data
US 2020/0333965 A1  Oct. 22, 2020

Related U.S. Application Data

(60) Provisional application No. 62/574,687, filed on Oct. 19, 2017.

(51) Int. Cl.
*G06F 3/06* (2006.01)
*A61B 8/12* (2006.01)
*A61B 8/00* (2006.01)

(52) U.S. Cl.
CPC .............. *G06F 3/0622* (2013.01); *A61B 8/12* (2013.01); *A61B 8/56* (2013.01); *G06F 3/0652* (2013.01);
(Continued)

(58) Field of Classification Search
CPC .... G06F 3/0622; G06F 3/0652; G06F 3/0659; G06F 3/0679; A61B 8/12; A61B 8/56;
(Continued)

(56) References Cited

U.S. PATENT DOCUMENTS 7,089,427 B1 * 8/2006 Takata ..................... G11C 7/24
463/43
9,101,298 B2 8/2015 Hossack
(Continued)

FOREIGN PATENT DOCUMENTS

WO 2019076968 A1 4/2019
WO 2019077141 A1 4/2019

OTHER PUBLICATIONS

International Search Report & Written Opinion of PCT/EP2018/078381, dated Feb. 18, 2019.

*Primary Examiner* — Kalpit Parikh

(57) ABSTRACT

A sensing system includes a patient interface module (PIM) communicatively disposed between a processing system and a sensing device configured to obtain measurement data associated with a body of a patient while positioned within the body, the sensing device comprising a memory, wherein the patient interface module comprises: a controller operable to: read data stored on the memory of the sensing device using a first signal voltage; and write to the memory to disable further operation of the sensing device using a second signal voltage; and a voltage switch configured to selectively output the first signal voltage or the second signal voltage.

24 Claims, 6 Drawing Sheets

(52) U.S. Cl.
CPC .......... *G06F 3/0659* (2013.01); *G06F 3/0679* (2013.01); *A61B 2560/0475* (2013.01)

(58) Field of Classification Search
CPC .......... A61B 8/0891; A61B 2560/0475; A61B 2090/0803; B06B 1/0207; B06B 2201/76
See application file for complete search history.

(56) References Cited

U.S. PATENT DOCUMENTS

| | | | |
|---|---|---|---|
| 9,445,723 | B2 | 9/2016 | Hoffman |
| 2006/0010302 | A1* | 1/2006 | Yamamoto .............. G06F 21/77 |
| | | | 711/163 |
| 2006/0161054 | A1 | 7/2006 | Reuss |
| 2007/0083111 | A1 | 4/2007 | Hossack |
| 2009/0097345 | A1* | 4/2009 | Kushnarenko ......... G11C 29/14 |
| | | | 365/201 |
| 2013/0103023 | A1 | 4/2013 | Monson |
| 2014/0276603 | A1* | 9/2014 | Magee ................... A61B 90/90 |
| | | | 604/95.01 |
| 2014/0343433 | A1* | 11/2014 | Elbert ...................... A61B 8/54 |
| | | | 600/467 |
| 2017/0215699 | A1 | 8/2017 | Ouyang |
| 2019/0117191 | A1 | 4/2019 | Hoffman |

* cited by examiner

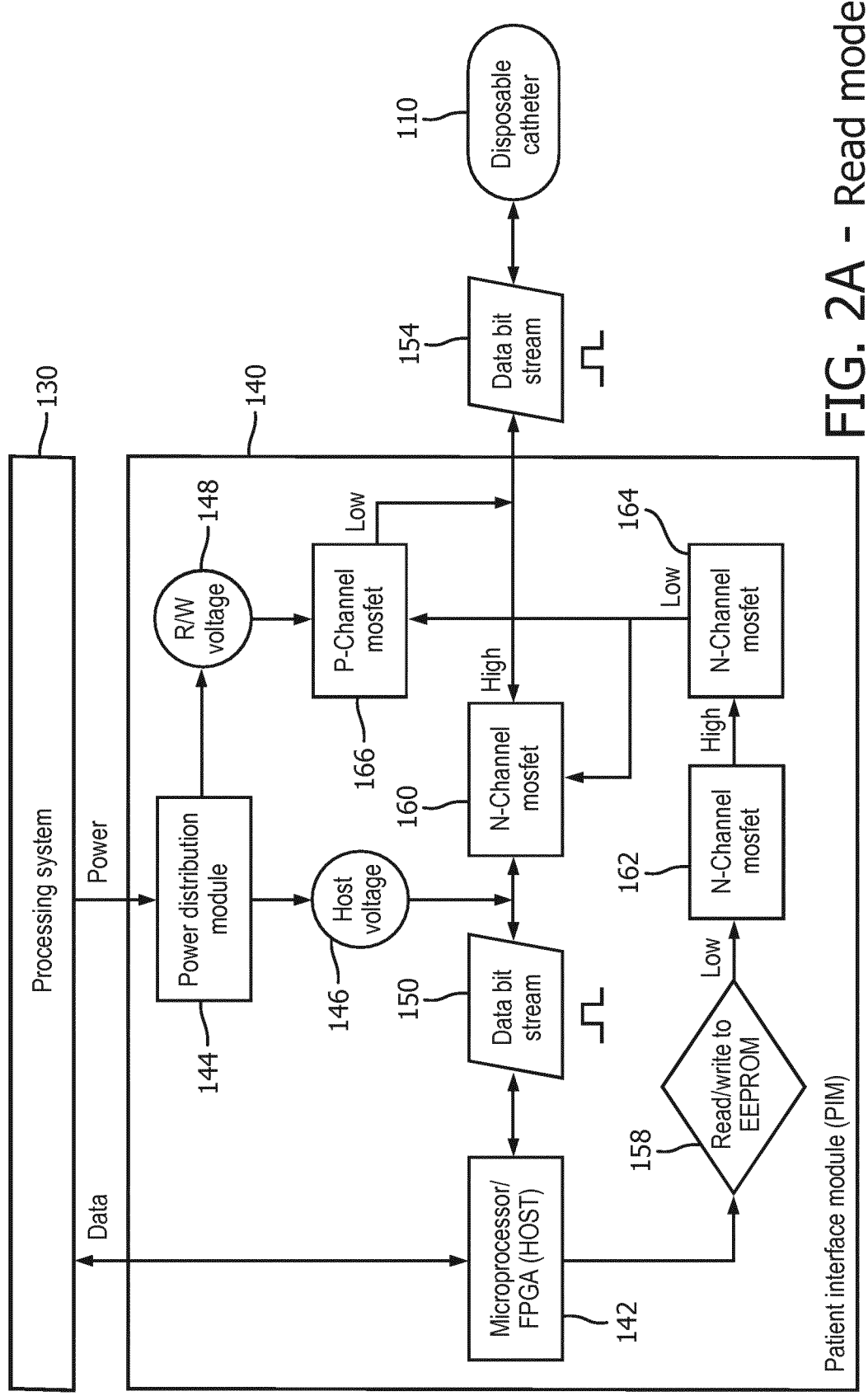
FIG. 2A - Read mode

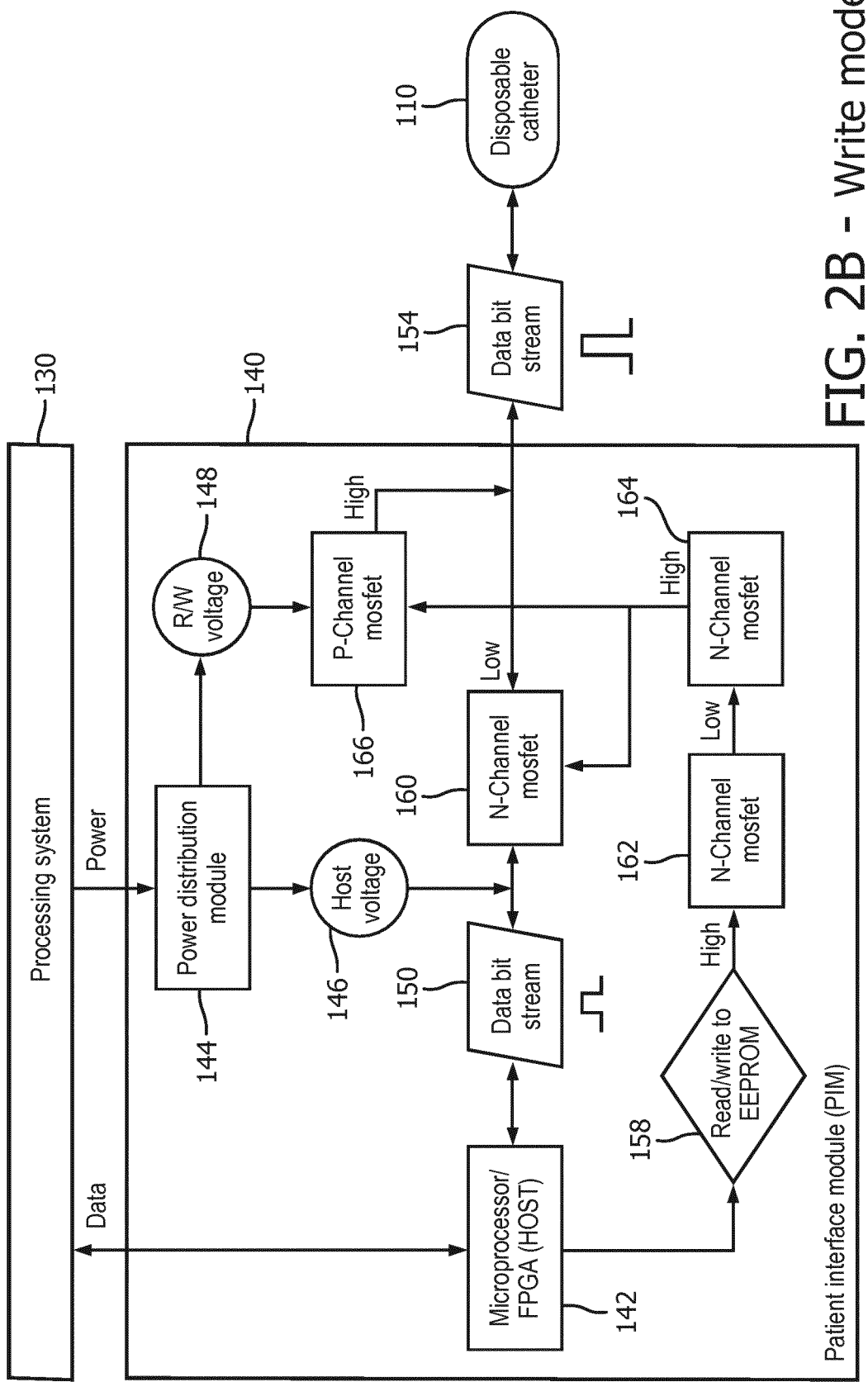
FIG. 2B - Write mode

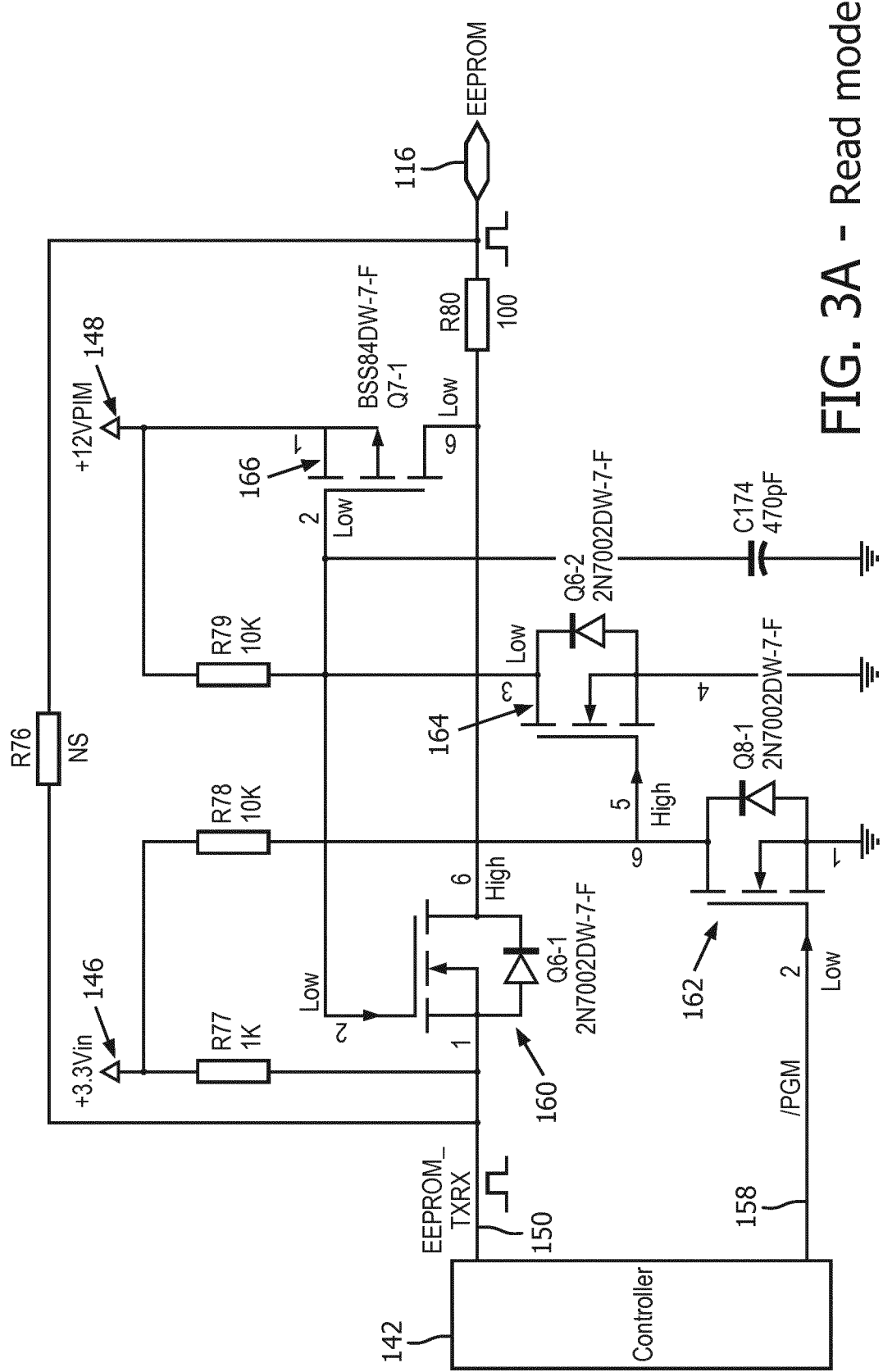
FIG. 3A - Read mode

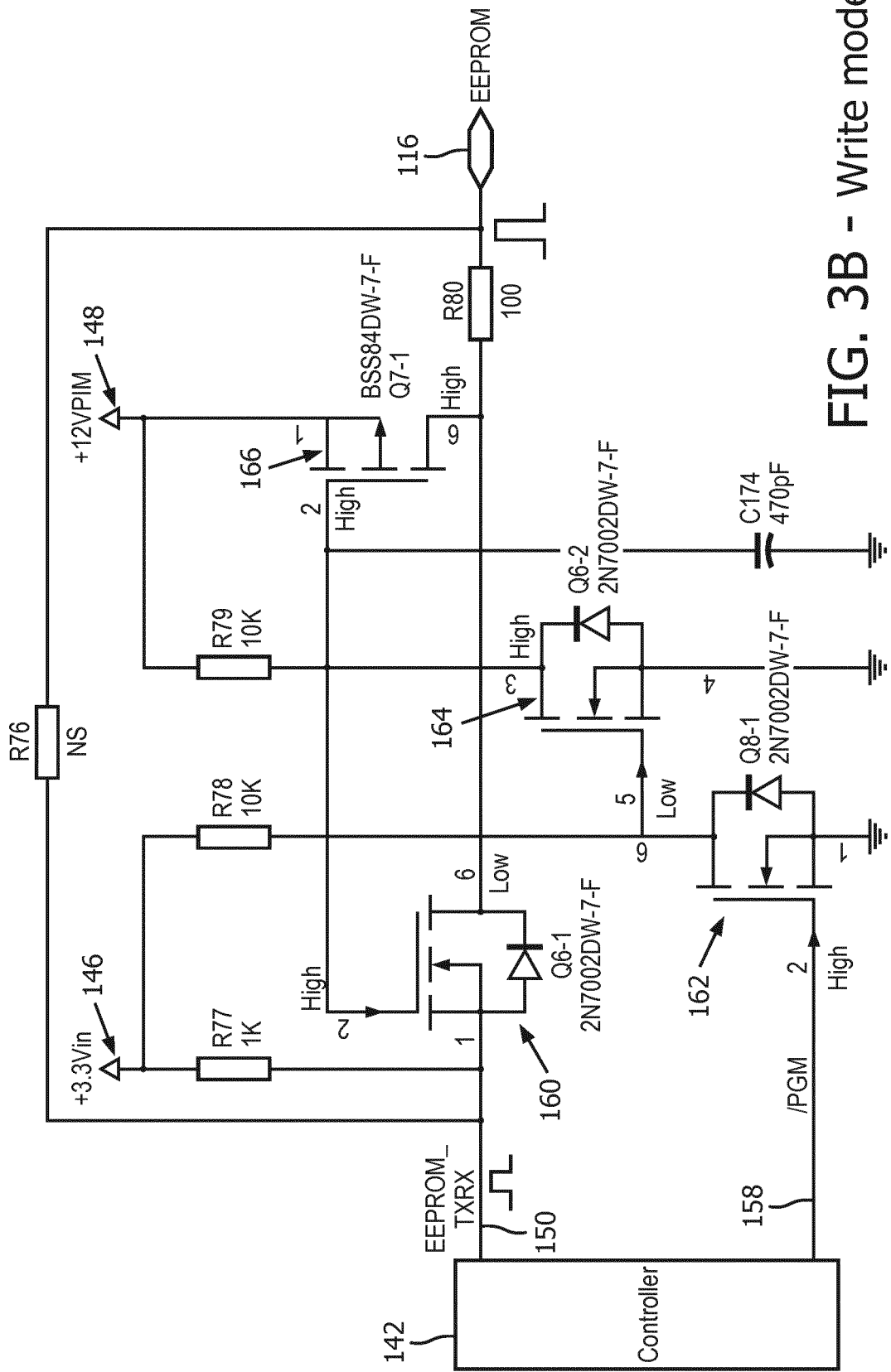
FIG. 3B - Write mode

INTRALUMINAL DEVICE REUSE PREVENTION WITH PATIENT INTERFACE MODULE AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2018/078381, filed on Oct. 17, 2018, which claims the benefit of U.S. Provisional Patent Application No. 62/574,687, filed on Oct. 19, 2017. These applications are hereby incorporated by reference herein.

TECHNICAL FIELD

The present disclosure relates generally relates to disabling subsequent use of a disposable, single-use intraluminal sensing device with at patient interface module (PIM). For example, the intraluminal sensing device can include a memory, and the PIM can write to the memory to disable further operation of the intraluminal sensing device after it has been used in a clinical procedure.

BACKGROUND

Intravascular devices, such as guide wires, catheters, guide catheters, etc., can be configured for imaging, flow measurement, and/or pressure measurement, among other functions. Such intravascular devices are generally disposable devices. Further, a manufacturer generally rates the intravascular device for a single use. That is, the manufacturer guarantees the safety of the intravascular device and/or the integrity of the data collected using the intravascular device for a single use. After being used within the vasculature of a patient in a clinical procedure, the intravascular device is discarded.

Recently, third parties that are not authorized by the manufacturer have collected used intravascular devices. The used intravascular devices are then sterilized, repackaged, and sold for future use in clinical procedures. This presents significant risk to patients. These intravascular devices have not been verified and validated, and therefore cannot be guaranteed or expected to meet the necessary safety and efficacy standards of an authentic intravascular device. When an intravascular device is inappropriately reused, it can expose patients to direct harm via contamination. It can also expose patients to the possibility of misdiagnosis when a disposable intravascular device is used for a longer time than it was designed to operate safely. In addition to patient safety concerns, a manufacturer also suffers financial losses when customers purchase repackaged, used intravascular devices as opposed to authorized ones.

SUMMARY

Embodiments of the present disclosure provide a way to prevent authorized reuse of a single use intraluminal device, such as an intravascular catheter or guidewire. A patient interface module (PIM) is communicatively positioned between a console/processing system and an intraluminal device. The intraluminal device includes a memory. The PIM is able to selectively transmit read commands at a first signal voltage and write commands at a second signal voltage to the memory of the intraluminal device. The PIM selectively outputs the first voltage or the second voltage using a voltage switch including a plurality of electronic components, such as transistors.

In another exemplary aspect, the present disclosure is directed to an intraluminal sensing system. The system includes a patient interface module (PIM) communicatively disposed between a processing system and an intraluminal sensing device configured to obtain physiology data associated with a body lumen of a patient while positioned within the body lumen, the intraluminal sensing device comprising a memory, wherein the patient interface module comprises: a controller operable to: read data stored on the memory of the intraluminal sensing device using a first signal voltage; and write to the memory to disable further operation of the intraluminal sensing device using a second signal voltage; and a voltage switch configured to selectively output the first signal voltage or the second signal voltage.

In an aspect, the voltage switch comprises a plurality of electronic components. In an aspect, the plurality of electronic components comprises a plurality of transistors. In an aspect, the plurality of transistors comprises a plurality of metal-oxide-semiconductor field-effect transistors (MOSFETs). In an aspect, the plurality of MOSFETs comprises a p-channel MOSFET and a plurality of n-channel MOSFETs. In an aspect, the second signal voltage is associated with a command to erase the memory. In an aspect, the second signal voltage is associated with a command to write a date stamp to the memory. In an aspect, the date stamp is representative of a use date of the intraluminal sensing device to obtain the physiology data. In an aspect, the memory comprises an EEPROM. In an aspect, the system further includes the intraluminal sensing device; and the processing system.

In an exemplary aspect, the present disclosure is directed to a method of preventing unauthorized use of an intraluminal sensing device. The method includes reading, using a controller of a patient interface module (PIM) communicatively disposed between a processing system and an intraluminal sensing device configured to obtain physiology data associated with a body lumen of a patient while positioned within the body lumen, data stored on a memory of the intraluminal sensing device using a first signal voltage; and modifying a voltage of an output signal using a voltage switch of the PIM; and writing to the memory to disable further operation of the intraluminal sensing device using a second signal voltage.

In an aspect, the voltage switch comprises a plurality of electronic components. In an aspect, the plurality of electronic components comprises a plurality of transistors. In an aspect, the plurality of transistors comprises a plurality of metal-oxide-semiconductor field-effect transistors (MOSFETs). In an aspect, the plurality of MOSFETs comprises a p-channel MOSFET and a plurality of n-channel MOSFETs. In an aspect, the writing to the memory comprises transmitting a command to erase the memory. In an aspect, the writing to the memory comprises transmitting a command to write a date stamp to the memory. In an aspect, the date stamp is representative of a use date of the intraluminal sensing device to obtain the physiology data. In an aspect, the memory comprises an EEPROM.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 2A is a diagrammatic schematic view of an intraluminal sensing system in a read mode, including a patient interface module (PIM), according to aspects of the present disclosure.

FIG. 2B is a diagrammatic schematic view of an intraluminal sensing system in a write mode, including a PIM, according to aspects of the present disclosure.

FIG. 3A is an electrical circuit diagram of a PIM in a read mode, according to aspects of the present disclosure.

FIG. 3B is electrical circuit diagram of a PIM in a write mode, according to aspects of the present disclosure.

DETAILED DESCRIPTION

Figure 1:
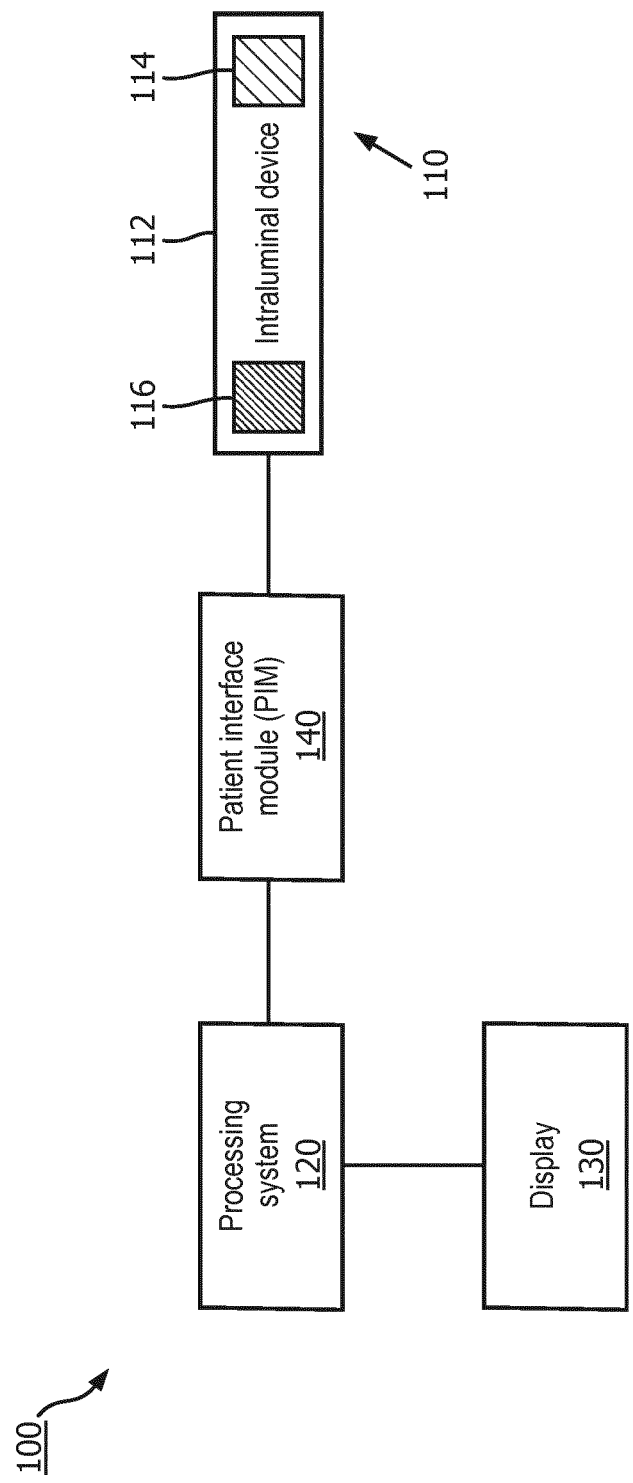
FIG. 1 is a diagrammatic schematic view of an intraluminal sensing system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The devices, systems, and methods described herein relate to a patient interface module (PIM) having the ability to read and write to a memory of a disposable catheter or guide wire, preventing the reuse of that device. An aspect of the present disclosure includes reading and/or writing to the EEPROM via a bidirectional bit stream set by changing the pull-up voltage through the use of MOSFET switching. This selectively transmits the required "read" voltage or the "write" voltage to the EEPROM.

Aspects of the present disclosure including writing to the EEPROM on the disposable intraluminal device to erase sensitive data stored on the memory of the device, preventing the device from reuse and its proprietary information from being accessed. The reuse prevention architecture using a read and write capability advantageously prevents reuse of the intraluminal device and/or access to the sensitive material stored on the memory of the intraluminal device by a third party. The general architecture for reuse prevention design includes a microprocessor or FPGA (host) capable of programming the EEPROM using a single bidirectional signal line to communicate the "read" and "write" commands by either the same voltage or different voltages. The read voltage can be set at the host side by an n-channel MOSFET. The write voltage is set by a p-channel MOSFET. Selectively outputting the read voltage or the write voltage is controlled by voltage switch, including one or more n-channel MOSFETs and one or more p-channel MOSFETs. The read voltage or the write voltage is set by the MOSFETs switching "gate" pin. The host controls the output data communication set voltage depending on the EEPROM's characteristic of a "read" or "write" command. The host can set an operational time stamp for use, erase the EEPROM preventing access to and/or removing proprietary catheter data, e.g., as an option to avoid quick catheter disconnect. In some embodiments, creating a time stamp on the disposable intraluminal device, based on a command by a processor of the PIM, and sending a write command by the serial bit stream advantageously creates an actual disposable device after the device has been use in a medical procedure.

The devices, systems, and methods of the present disclosure advantageously facilitate patient safety by preventing unauthorized reuse of intraluminal devices which that are not rated from multiple uses. Also, financial losses to the manufacturer of the single-use intraluminal device are advantageously reduced.

FIG. 1 is a diagrammatic schematic view of an intraluminal system 100, according to aspects of the present disclosure. The intraluminal system 100 includes an intraluminal device 110, a processing system 120, a display 130, and a patient interface module (PIM) 140.

The intraluminal device 110 can include a flexible elongate member 112, a sensor 114 disposed at the distal portion of the flexible elongate member 112, and a memory 116 disposed at the proximal portion of the flexible elongate member 112. In some embodiments, the intraluminal device can be a catheter, a guide wire, and/or a guide catheter. Generally, the intraluminal device 110 can be size and shaped, structurally arranged, and/or otherwise configured to be positioned within anatomy, such as a body lumen, of a patient. The anatomy may represent any fluid-filled or surrounded structures, both natural and man-made. For example, the anatomy can be within the body of a patient. Fluid can flow through the lumen of the anatomy. The anatomy can be a vessel, such as a blood vessel, in which blood flows through the lumen of the vessel. For example, the intraluminal device can be an intravascular device and the intraluminal system can be an intravascular system. In various embodiments, the blood vessel is an artery or a vein of a patient's vascular system, including cardiac vasculature, peripheral vasculature, neural vasculature, renal vasculature, and/or any other suitable anatomy/lumen inside the body. The anatomy can be tortuous in some instances. For example, the device 110 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 110 may be used to examine man-made structures such as, but without limitation, heart valves, stents, shunts, filters and other devices.

In some embodiments, the intraluminal device 110 is configured to image the body lumen of a patient (e.g., a lumen of a blood vessel) using one or more imaging modalities. For example, the sensing component 114 can be an imaging component. In some embodiments, the sensor 114 is an ultrasound transducer and/or an ultrasound transducer array. For example, the intraluminal device 110 can be an intravascular ultrasound or IVUS imaging device. The intraluminal device can be a rotational IVUS imaging device including a rotating drive cable that rotates one or more ultrasound transducers at the distal portion of the flexible elongate member 112. The intraluminal device can be a phased array IVUS imaging device including a circumferential/annular transducer array around a longitudinal axis. In various embodiments, the sensor 114 can obtain imaging data associated with intravascular ultrasound (IVUS) imaging, forward-looking intravascular ultrasound (FL-IVUS) imaging, intravascular photoacoustic (IVPA) imaging, intracardiac echocardiography (ICE), forward-looking intracardiac echocardiography (FLICE), transesophageal echocardiography (TEE), and/or other suitable imaging modalities. In some embodiments, the device 110 can include an imaging component of any suitable imaging modality, such as optical imaging, optical coherence tomography (OCT), etc.

In some embodiments, the device 110 can include any suitable sensing component 114, including a pressure sensor, a flow sensor, a temperature sensor, an optical fiber, a reflector, a mirror, a prism, an ablation element, a radio frequency (RF) electrode, a conductor, and/or combinations thereof. The intraluminal device 110 can include one or more sensing components 114. Generally, the sensor 114 can be an electronic component, an optical component, an acoustic component, and/or combinations thereof.

The intraluminal device 110 includes a memory 116. The memory 116 can be a rewritable/reprogrammable memory that can be rewritten or reprogrammed, after being initially programmed during manufacturing of the intraluminal device 110, without degradation of the memory and/or the intraluminal device 110. In some embodiments, the memory 116 can include one or more bits that determine whether the memory 116 can be read and/or accessed. For example, in response to command signal associated with the memory 116, and received from the processing system 120 and/or the PIM 140, the ability to read and/or access the memory 116 can be disabled, which prevents subsequent operation of the intraluminal device 110. In some embodiments, a command signal from the processing system 120 and/or the PIM 140 can erase the memory 116. In some embodiments, the processing system 120 and/or the PIM 140 can write a use date to the memory 116. The use date can be read by any suitable processing system and/or PIM upon subsequent use of the intraluminal device 110, which disallows operation of the intraluminal device 110.

In various embodiments, the memory 116 can be Electrically Erasable Programmable Read-Only Memory (EEPROM), flash memory, hard disk, RFID, and/or other suitable storage. In an exemplary embodiment, the storage capacity of the memory 116 can be 0.5 KB, 1 KB, 2 KB, and/or other suitable values, both larger and smaller. The memory 116 can be disposed on a proximal connector of the intraluminal device 110, as described in U.S. Pat. No. 9,101,298, titled "Apparatus and Method for Use of RFID Catheter Intelligence," the entirety of which is hereby incorporated by reference herein. The memory 116 has sufficient capacity to store data about the intraluminal device 110, such as a parameters associated with the sensing component 114 and/or the intraluminal device 110. For example, the memory 116 can be store data related to the catheter type, serial number, configuration for sensitivity, channel matching, ringdown parameters, catheter over-current indicator, and ramp-gain-control (RGC), selection for control of the timing voltage for the PIM's variable-gain-amplifier (VGA), etc.

In some instances, the data stored on memory 116 can be sensitive and/or proprietary information that a manufacturer of the intraluminal device 110 would not want a third party or competitor to access. As described herein, access to the memory 116 by a third party or competitor is advantageously prevented.

The intraluminal device 110 is a disposable or limited use device. For example, a manufacturer can guarantee the safety of the intraluminal device 110 and/or the integrity of the data collected using the intraluminal device 110 for a single use, in some embodiments. As described herein, unauthorized reuse (e.g., subsequent use after a first use of the intraluminal device 110 to obtain intraluminal data) of the intraluminal device 110 is advantageously prevented. In other embodiments, the intraluminal device 110 can be used in multiple procedures, after the manufacturer or authorized third-party has sterilized and/or reconditioned the intraluminal device 110, as described in U.S. Pat. No. 9,445,723, titled "Devices, Systems and Methods for Authenticated Intravascular Device Use and Reuse," the entirety of which is hereby incorporated by reference herein.

The system 100 includes a processing system or console 120 that is in communication with the intraluminal device 110 via the PIM 140. The computing device 120 can include a processing circuit, such as one or more processors in communication with a memory. The computing device 120 can control the intraluminal device 110 and/or the PIM 140 to obtain medical data associated with the anatomy in which the intraluminal device 110 is positioned. For example, the system 100 can include an input device, such as a keyboard, mouse, controller with buttons, touchscreen, touchpad, etc., in communication with the computer 120. In response to a user input by a user, such as a physician or other medical professional, at the input device, the computer 120 can output command signals to the PIM 140 and/or the intraluminal device 110 to, e.g., start/stop acquisition of the intraluminal data. In some embodiments, when an intraluminal device 110 is connected to the PIM 140, the processing system 120 and/or the PIM 140 transmits a signal to read the memory 116 of the intraluminal device 110. The intraluminal device 110 can transmit data stored on the memory 116, such as the identity of the device 110, the sensor type of the sensor 114, etc., to the PIM 140 and/or the processing system 120. The intraluminal device 110 and/or the PIM 140 can transmit data signals to the processing system 120. For example, electrical signals representative of the physiology data obtained by the sensing component 114 can be transmitted from the intraluminal device 110 to the processing system 120 via the PIM 140. The processing system 120 can be configured to process the received data, generate a visual representation of the obtained data, and output the visual representation of the obtained data to the display 130. In some embodiments, the input device, the display 130, and/or the processing system 120 can be separate components. In other embodiments, one or more of the input device, the display 130, and/or the processing system 120 can be combined or be a single component.

The system includes the PIM 140 communicatively positioned between the processing system 120 and the intraluminal device 110. As described herein, the PIM 140 is configured to write to the memory 116 to prevent unauthorized reuse of the intraluminal device 110. The PIM 140 facilitates communication of signals between the console 120 and the intraluminal device 110. In some embodiments, the PIM 140 supplies high- and/or low-voltage DC power to support operation of the intravascular device 110, including the component(s) 114 for imaging, pressure measurement, and/or flow measurement. In some embodiments, the PIM 140 is configured to access, read, and/or write the memory 116 based on, e.g., instructions from the processing system 120. In other embodiments, the processing system 120 is configured to directly access, read, and/or write the memory 116 without the PIM 140. The PIM 140 can comprise a housing having any suitable shape. The PIM 140 can include a volume (e.g., a length, a width, a depth, a radius, etc.)

within the housing configured to accommodate one or more components described herein. The PIM 140 can be sized and shaped, structurally arranged, and/or otherwise configured for handheld use in some embodiments.

In some embodiments, the PIM 140 can include features similar to those described in U.S. Patent Application No. 62/574,455, titled "DIGITAL ROTATIONAL PATIENT INTERFACE MODULE," filed Oct. 19, 2017, U.S. Patent Application No. 62/574,655, titled "WIRELESS DIGITAL PATIENT INTERFACE MODULE USING WIRELESS CHARGING," filed Oct. 19, 2017, U.S. Patent Application No. 62/574,835, titled "INTRALUMINAL MEDICAL SYSTEM WITH OVERLOADED CONNECTORS," filed Oct. 20, 2017, and U.S. Patent Application No. 62/574,610, titled "HANDHELD MEDICAL INTERFACE FOR INTRALUMINAL DEVICE AND ASSOCIATED DEVICES, SYSTEMS, AND METHODS," filed Oct. 19, 2017, each of which is incorporated by reference in its entirety.

FIGS. 2A, 2B, 3A, and 3B illustrate additional aspects of the system 100 and/or the PIM 140. FIGS. 2A and 2B are diagrammatic schematic views of the intraluminal sensing system 100, including the patient interface module 140. FIGS. 3A and 3B are electrical circuit diagrams of the PIM 140. FIGS. 2A and 3A illustrate the system 100 and/or the PIM 140 in a read mode. FIGS. 2B and 3B illustrate the system 100 and/or the PIM 140 in a write mode.

Referring to FIGS. 2A and 2B, the processing system 120 transmits power to a power distribution module 144 of the PIM 140. The power distribution module 144 distributes power received from the processing system 120 to various components of the PIM 140 (e.g., a processor 142, a transmitter associated with an ultrasound transducer of the intraluminal device 110, etc.). The power transmitted by the processing system 120 has a voltage, such as 5V, 10V, 12V, 15V, 20V, 40V, and/or other suitable value, both larger and smaller, for example. The power distribution module 144 is configured to distribute power to the various components of the PIM 140 at various voltages, which may be the same or different than the voltage transmitted by the processing system 120 to the PIM 140. For example, the host voltage 146 and/or the read/write voltage 148 can be the same or different than the voltage transmitted by the processing system 120 to the PIM 140. The host voltage 146 can be the same or different than the read/write voltage 148. In some embodiments, the host voltage 146 and/or the read/write voltage 148 can be 1V, 2V, 3V, 5V, 10V, 12V, 15V, and/or other suitable value, both larger and smaller.

Referring to FIGS. 2A, 2B, 3A, and 3B, the PIM 140 includes a processing component 142. The processing component 142 can be a microprocessor. In some embodiments, the processing component 142 is a field programmable gate (FPGA). The processing component 142 can be referenced as a host in some instances. The processing component 142 can be one or more processors configured to receive electrical signals representative of data from and/or transmit electrical signals representative of data to the processing system 120 and/or the intraluminal device 110. For example, the processor or controller 142 can transmit data bit stream 150, 154 to the intraluminal device 110 to, e.g., read or write to the memory 116. The data bit stream 150, 154 can be an electrical signal that includes an amplitude or voltage, frequency, timing, sequence, and/or other characteristics. Read signals from the PIM 140 to the memory 116 can be a first signal voltage, and write signals from the PIM 140 to the memory 116 can be a second signal voltage. In some embodiments, the first and second signal voltages are the same. In some embodiments, the first and second signal voltages are different.

The PIM 140 includes a voltage or power switch. As described below, the voltage or power switch can include one or more electronic components, such as one or more metal-oxide-semiconductor field-effect transistors (MOSFETs). The voltage or power switch can be electrically disposed between the processor 142 and the output of the PIM 140 such that the voltage or power switch selectively determines the voltage of the output signal from the PIM 140 to the intraluminal device 110. In that regard, the voltage or power switch determines whether output voltage of the PIM 140 should be host voltage 146 and/or the output voltage of the processor 142, or whether the output voltage of the PIM 140 should be the read/write voltage 148.

Illustrations of exemplary electrical signals associated with the data bit streams 150, 154 are shown in FIGS. 2A, 2B, 3A, and 3B. In FIGS. 2A and 3A, the amplitude or voltage of the exemplary electrical signal is same for both the data bit stream 150 output by the processor 142 and the data bit stream 154 that is output from the PIM 140 to the intraluminal device 110. FIGS. 2A and 3A illustrate a read mode in which the data bit streams 150, 154 allow the processor 142 to read the memory 116, for example, in response to a command from the processing system 120. In an embodiment, the voltage of the data bit streams 150, 154 of FIGS. 2A and 3A is the host voltage 146. For example the host voltage 146, and the voltage of the data bit streams 150, 154 of FIGS. 2A and 3A is 3V.

The voltage or power switch of the PIM 140 is configured to determine and/or to change the output signal voltage of the PIM 140. In FIGS. 2B and 3B, the amplitude or voltage of the exemplary electrical signal associated with the data bit stream 150 output by the processor 142 is different than the amplitude or voltage of the exemplary electrical signal associated with the data bit stream 154 that is output from the PIM 140 to the intraluminal device 110. FIGS. 2B and 3B illustrate a write mode in which the data bit streams 150, 154 allow the processor 142 to write to the memory 116, for example, in response to a command from the processing system 120. In that regard, the processing system 120 and/or the processor 142 can write one or more bits to the memory 116 to lock, and/or otherwise disallow further reading of the memory 116. For example, the processing system 120 and/or the processor 142 can write one or more bits to the memory 116 to erase the memory 116. In another example, the processing system 120 and/or the processor 142 can write one or more bits to the memory 116 associated with a time stamp, e.g., representative of the use of the intraluminal device 110. In an embodiment, the voltage of the data bit stream 150 is the host voltage 146, while, in FIGS. 2B and 3B, the voltage of the data bit stream 154 is the read/write voltage 148. That is, the voltage or power switch of the PIM 140 is disposed between the processor 142 and the output of the PIM 140 such that the voltage or power switch selectively determines the voltage of the output signal from the PIM 140. For example, the host voltage 146 and/or the voltage the data bit stream 150 can be 3V, while the read/write voltage 148 and/or the voltage of the data bit stream 154 is 12V in in FIGS. 2B and 3B. In an exemplary embodiment, the voltage or power switch modifies only the amplitude or voltage of the electrical signal output. For example, the frequency, timing, sequence, and/or other characteristics of the electrical signal remain the same between the signal output by the processor 142 and the PIM 140.

Referring to FIGS. 2A, 2B, 3A, and 3B, the voltage or power switch of the PIM 140 can include one or more electronic components 160, 162, 164, 166. For example, the electronic components 160, 162, 164, 166 can be one or more transistors. In some embodiments, the transistors can be a bipolar junction transistor (BJT), a field-effect transistor (FET), other suitable transistor type, and/or combinations thereof. In some examples, the transistor can be a p-channel transistor or an n-channel transistor. In some embodiments, the electronic components 160, 162, 164, 166 can be one or more junction field effect transistors (JFETs) or metal-oxide-semiconductor field-effect transistors (MOSFETs). In some instances, the transistor can be a depletion-mode and enhancement-mode transistor. Generally, the voltage or power switch of the PIM 140 can include one, two, three, four, five, or more electronic components 160, 162, 164, 166. In the illustrated embodiment, the PIM 140 includes four MOSFETs, including three n-channel MOSFETs 160, 162, 164 and one p-channel MOSFET 166. Generally, the PIM 140 can include an even or odd number of MOSFETs, including an one or more n-channel MOSFETs (e.g., an even or odd number) and one or more p-channel MOSFETs (e.g., an even of odd number).

The MOSFETs 160, 162, 164, 166 are arranged in communication with one another, the processor 142, and/or the memory 116 of the intraluminal device 110 such that the PIM 140 outputs the host voltage 146 (e.g., 3V) or the read/write voltage 148 (e.g., 12V) to the memory 116 of the intraluminal device 110. For example, the n-channel MOSFET 160 is electrically and/or communicatively disposed between the processor 142 and the memory 116. The n-channel MOSFET 162 is electrically and/or communicatively disposed between the processor 142 and n-channel MOSFET 164. The n-channel MOSFET 164 is electrically and/or communicatively disposed between the n-channel MOSFET 162, n-channel MOSFET 160, and the p-channel MOSFET 166.

The processor 142 transmits the data bit stream 150 including one or more bits that are representative of the command to the memory 116 and/or the intraluminal device 110. As described herein, the voltage or power switch determines the output signal voltage of the PIM 140, which is represented by data bit stream 154. The processor 142 transmits a read/write signal 158 to the n-channel MOSFET 162. For example, the read/write signal 158 can be transmitted by the processor in response to a signal to do from the processing system 120. The read/write signal 158 can be one or more bits indicating whether the PIM will read the memory 116 or write to the memory 116. For example, the read/write signal 158 can be a single bit, such as a 1 (high) or 0 (low).

In the read-mode of FIGS. 2A and 3A, the read/write signal 158 is low. The low read/write signal 158 is the input of the n-channel MOSFET 162. N-channel MOSFETs invert the signal from low to high or high to low. Accordingly, the output signal of the n-channel MOSFET 162 and the input signal of the n-channel MOSFET 164 is high. The output signal of the n-channel MOSFET 164 is low. Accordingly, the input signal of the n-channel MOSFET 160 and the input signal of the p-channel MOSFET is low. P-channel MOSFETs maintain, rather than invert, the signal such that a high signal is maintained as high and a low signal is maintained as low. Accordingly, the output signal of the p-channel MOSFET 166 is low. The output signal of the n-channel MOSFET 160 is high. The n-channel MOSFET 160 is in communication with the host voltage 146 such that when the output of the n-channel MOSFET 160 is high, the data bit stream 154 has the host voltage 146. When input signal is low on n-channel MOSFET 160, the host voltage 146 will be present on the memory 116. As shown in FIG. 3A, when the signal on pin 2 of n-channel MOSFET 160 goes low, the data will go from n-channel MOSFET 160 pin 1 to pin 6. This also causes p-channel MOSFET 166 to shut off, and sends the read/write voltage 148 from p-channel MOSFET 166 pin 1 to pin 2 down to the capacitor C174. This creates a read to the EEPROM 116. The p-channel MOSFET is in communication with read/write voltage 148 such that when the output of the p-channel MOSFET is low, the data bit stream 154 does not have the read/write voltage 148 (e.g., 12V). As shown in FIG. 3A, when the input signal of the p-channel MOSFET 166 is low, the read/write voltage 148 (e.g., 12V) is not transmitted across p-channel MOSFET 166 to the memory 116.

In the write-mode of FIGS. 2B and 3B, the read/write signal 158 is high. The high read/write signal 158 is the input of the n-channel MOSFET 162. Accordingly, the output signal of the n-channel MOSFET 162 and the input signal of the n-channel MOSFET 164 is low. The output signal of the n-channel MOSFET 164 is high. Thus, the input signal of the n-channel MOSFET 160 and the input signal of the p-channel MOSFET is high. Therefore, the output signal of the p-channel MOSFET 166 is high. The output signal of the n-channel MOSFET 160 is low. The p-channel MOSFET is in communication with read/write voltage 148 such that when the output of the p-channel MOSFET is high, the data bit stream 154 has the read/write voltage 148 (e.g., 12V). As shown in FIG. 3B, when the input signal of the p-channel MOSFET 166 is high, the read/write voltage 148 (e.g., 12V) is transmitted across p-channel MOSFET 166 using pins 1 and 6 to the memory 116. The signal on the gate pin on the p-channel MOSFET 166 determines if the output signal of the PIM 140 is the read/write voltage 148 or the host voltage 146, from the n-channel MOSFET 160. Correspondingly, the n-channel MOSFET 160 is in communication with the host voltage 146 such that when the output of the n-channel MOSFET 160 is low, the data bit stream 154 does not have the host voltage 146. When input signal is high on n-channel MOSFET 160, the read/write voltage 148 will be present on the memory 116. As shown in FIG. 3B, this causes the host voltage 146 and data to go from n-channel MOSFET pin 1 to pin 2, and then to p-channel MOSFET 166 pin 2 to pin 6. This creates a write to the EEPROM.

The input signal and/or output signal of the n-channel MOSFET 164, the n-channel MOSFET 160, and/or the p-channel MOSFET 166 can determine the output signal voltage of the PIM 140 (e.g., the data bit stream 154) in some embodiments.

The PIM 140 and/or the voltage switch of the PIM 140 can include one or more electronic components, such as one or more resistors and/or capacitors in communication with the MOSFETs 160, 162, 164, 166, the host voltage 146, and/or the read/write voltage 148.

The n-channel MOSFET 160 is communicatively arranged to prevent the read/write voltage 148 from being transmitted to the processor 142. In that regard, the processor 142 is configured to only operate at the host voltage 146, in some embodiments. The n-channel MOSFET 160 advantageously isolates the processor 142 from the read/write voltage 148, which can be transmitted to the intraluminal device 110.

Figure 4:
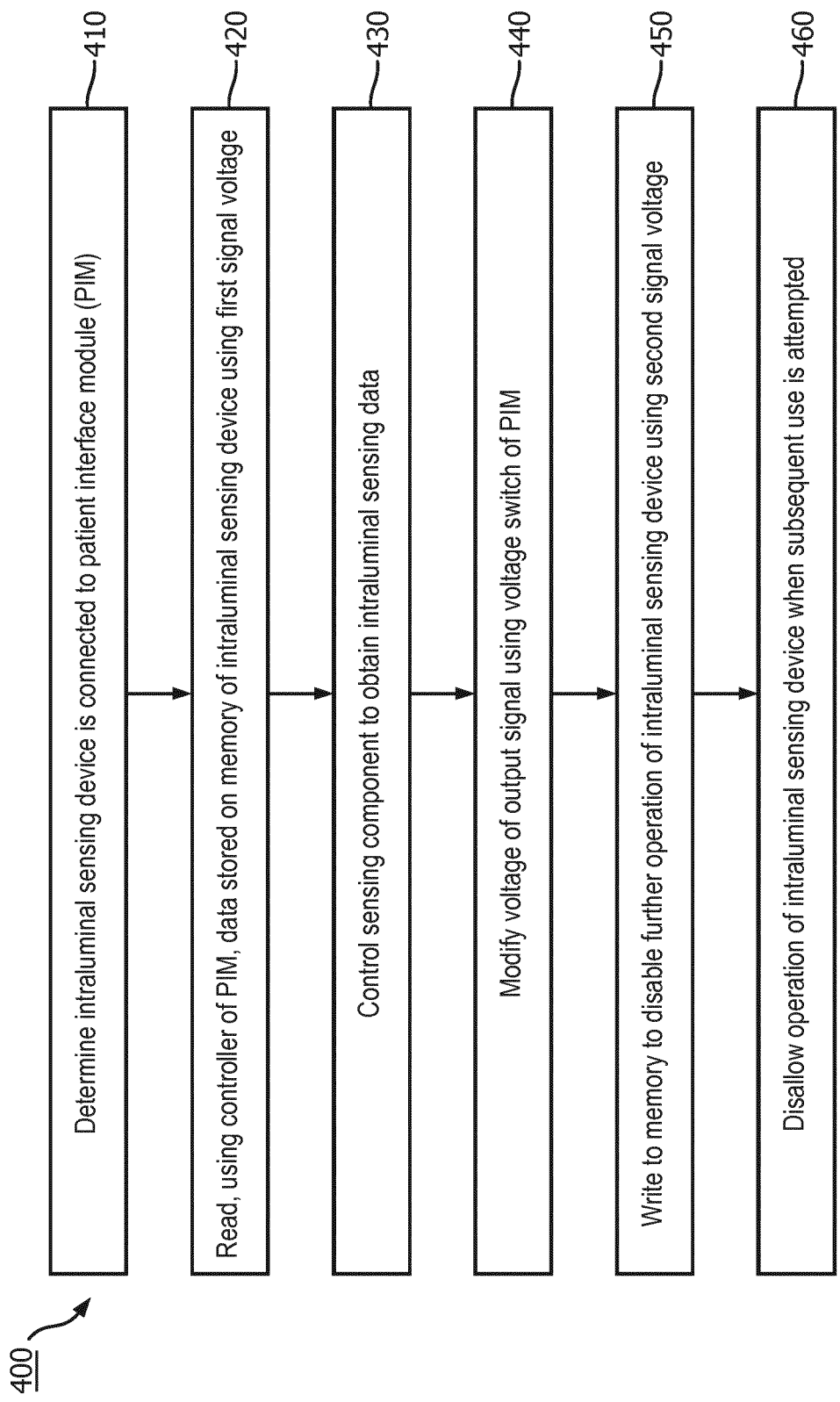
FIG. 4 is a flow diagram of a method for preventing unauthorized use of an intraluminal sensing device, according to aspects of the present disclosure.

FIG. 4 provides a flow diagram illustrating a method 400 of preventing unauthorized use of an intraluminal sensing device. As illustrated, the method 400 includes a number of enumerated steps, but embodiments of the method 400 may include additional steps before, after, and in between the enumerated steps. In some embodiments, one or more of the enumerated steps may be omitted, performed in a different order, or performed concurrently. The method 400 may be performed using one or more of the systems and devices referred to in FIGS. 1, 2A, 2B, 3A, and 3B.

At step 410, the method 400 includes determining an intraluminal sensing device is connected to the patient interface module (PIM). The intraluminal sensing device can include a memory, such as an EEPROM, and sensing component configured to obtain intraluminal sensing data associated with anatomy in which the intraluminal sensing device is positioned. At step 420, the method 400 includes reading, using a controller or processor of the PIM, data on the memory of the intraluminal sensing device. The controller can read the data using a first signal voltage. Step 420 can be performed by a console/processing system and/or the PIM, e.g., in response a command signal from the console/processing system. The PIM can be communicatively interposed between the console and the intraluminal sensing device. At step 430, the method 400 includes controlling the sensing device to obtain the intraluminal sensing data. For example, a control signal at the first voltage can be transmitted from the PIM to sensing component of the intraluminal device. Step 430 can be performed by a console/processing system and/or the PIM, e.g., in response a command signal from the console/processing system.

At step 440, the method 400 includes modifying the voltage of the output signal using a voltage or power switch of the PIM. In that regard, the voltage switch can include a plurality of electronic components, such as a plurality of transistors. The voltage switch can be configured to selectively output the first voltage or a second voltage from the PIM to the intraluminal sensing device. Step 440 can be performed by a console/processing system and/or the PIM, e.g., in response a command signal from the console/processing system. For example, a controller or processor of the PIM can transmit a command such that the voltage switch selectively determines whether the PIM outputs the first signal voltage or the second signal voltage.

At step 450, the method 400 includes writing to the memory of the intraluminal sensing device to disable further operation using the second signal voltage. For example, at the step 450, the memory of the intraluminal sensing device can be written to lock out or prevent further access to the memory. In some instances, the step 450 erases the memory. In other instances, the step 450 writes a date and/or time stamp, e.g., indicative of a use date and/or time of the intraluminal device. In still other instances, the step 450 writes any suitable data indicative of the usage of the intraluminal device. For example, the data written to the memory can be read by a console/processing system and/or a PIM as a day, month, year. In some embodiments, the data written to the memory can be a manufacturing lot unit built. A console/processing system and/or a PIM can recognize the manufacturing lot and disallow use when intraluminal devices associated with that manufacturing lot are beyond the period rated for use. Another example is writing the console/system's serial number with date code (e.g., use date), preventing the intraluminal device from use by another system. Step 440 can be performed by a console/processing system and/or the PIM, e.g., in response a command signal from the console/processing system. For example, the console/processing can transmit a command to the PIM to prevent further access to the memory of the intraluminal device using any suitable parameter. For example, the console can command the PIM to write to the memory to disable access, e.g., after a specified period of time (e.g., 10 minutes, 30 minutes, 60 minutes, 120 minutes, and/or other suitable values, both larger and smaller) post-commencement of a sensing procedure, post-completion of the sensing procedure, in response to a user input to end the collection of sensing data, when the sensing component 114 moves in a low power mode, prior to the intraluminal device 110 being unplugged, etc.

At step 460, the method 400 includes disallow operation of intraluminal sensing device when subsequent use is attempted. For example, a console or a PIM in a subsequent use attempt cannot read the memory of the intraluminal device because read access has been locked and/or the memory has been erased. In some instances, the console or the PIM read the date stamp or other indication of use stored on the memory. In response, the console and/or the PIM disallows subsequent operation of the intraluminal sensing device.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

While the present disclosure referred to primarily to intraluminal sensing devices, the system disclosed herein is well suited to authentication of any disposable or single use device, such as interventional devices for diagnosis or treatment (e.g. interventional needles, biopsy devices). The interventional devices substitute the intraluminal sensing devices in the system and method disclosed herein for the alternative embodiments. One skilled in the art will recognize the application of the principles herein across other disciplines.

What is claimed is:

1. A sensing system, comprising;
  a patient interface module (PIM) communicatively disposed between a processing system and a sensing device configured to obtain measurement data associated with a body of a patient while positioned within the body, the sensing device comprising a memory, wherein the patient interface module comprises:
    a controller operable to:
      output a first signal comprising a first voltage;
      output a different, second signal indicating a read operation for the PIM to read data stored on the memory or a write operation for the PIM to write to the memory; and
    a voltage switch, wherein the voltage switch configured to be responsive to the second signal such that:
      when the second signal indicates the read operation, the voltage switch maintains the first signal at the first voltage such that the PIM outputs the first signal at the first voltage to the memory to perform the read operation; and
      when the second signal indicates the write operation, the voltage switch modifies the first signal to have a different, second voltage such that the PIM outputs the first signal at the second voltage to the memory to perform the write operation.

2. The system of claim 1, wherein the voltage switch comprises a plurality of electronic components.

3. The system of claim 2, wherein the plurality of electronic components comprises a plurality of transistors.

4. The system of claim 3, wherein the plurality of transistors comprises a plurality of metal-oxide-semiconductor field-effect transistors (MOSFETs).

5. The system of claim 4, wherein the plurality of MOSFETs comprises a p-channel MOSFET and a plurality of n-channel MOSFETs.

6. The system of claim 1, wherein the second voltage is associated with a command to erase the memory.

7. The system of claim 1, wherein the second voltage is associated with a command to write a date stamp to the memory.

8. The system of claim 7, wherein the date stamp is representative of a use date of the sensing device to obtain the measurement data.

9. The system of claim 1, wherein the memory comprises an EEPROM.

10. The system of claim 1, further comprising:
the sensing device; and
the processing system.

11. The system of claim 10, wherein the sensing device is an intraluminal sensing device configured to obtain physiology measurement data associated with a body lumen of the patient while positioned within the body lumen.

12. The system of claim 1, wherein the voltage switch is communicatively disposed between the controller and the sensing device.

13. The system of claim 1,
wherein the controller is further operable to transmit, after the read operation is performed, a control signal to the sensing device to control the sensing device to obtain the measurement data,
wherein the write operation is configured to disable further operation of the sensing device, after the sensing device obtains the measurement data.

14. The system of claim 13, wherein the control signal uses the same voltage as the first voltage.

15. A method of preventing unauthorized use of a sensing device, the method comprising:
outputting, using a controller of a patient interface module (PIM) communicatively disposed between a processing system and the sensing device, a first signal comprising a first voltage, wherein the sensing device is configured to obtain measurement data associated with a body of a patient while positioned within the body;
outputting, using the controller, a different, second signal indicating a read operation for the PIM to read data stored on a memory of the sensing device or a write operation for the PIM to write to the memory;
in response to the second signal indicating the read operation:
maintaining, using a voltage switch of the PIM, the first signal at the first voltage; and
outputting, using the PIM, the first signal at the first voltage to the memory to perform the read operation; and
in response to the second signal indicating the write operation:
modifying, using the voltage switch, the first signal to have a different, second voltage; and
outputting, using the PIM, the first signal at the second voltage to the memory to perform the write operation.

16. The method of claim 15, wherein the sensing device is an intraluminal sensing device configured to obtain physiology measurement data associated with a body lumen of the patient while positioned within the body lumen.

17. The method of claim 15, wherein the voltage switch comprises a plurality of electronic components.

18. The method of claim 17, wherein the plurality of electronic components comprises a plurality of transistors.

19. The method of claim 18, wherein the plurality of transistors comprises a plurality of metal-oxide-semiconductor field-effect transistors (MOSFETs).

20. The method of claim 19, wherein the plurality of MOSFETs comprises a p-channel MOSFET and a plurality of n-channel MOSFETs.

21. The method of claim 15, wherein the performing the write operation comprises transmitting a command to erase the memory.

22. The method of claim 15, wherein the performing the write operation comprises transmitting a command to write a date stamp to the memory.

23. The method of claim 22, wherein the date stamp is representative of a use date of the sensing device to obtain the measurement data.

24. The method of claim 15, wherein the memory comprises an EEPROM.

* * * * *